(12) United States Patent
Panditrao et al.

(10) Patent No.: US 6,824,687 B2
(45) Date of Patent: Nov. 30, 2004

(54) EXTRACTION OF PHENOL FROM WASTEWATER

(75) Inventors: Sunil S. Panditrao, Wayne, NJ (US);
Amit Kelkar, Bloomfield, NJ (US);
Sanjeev Ram, Berkeley Heights, NJ (US); Ajay Gami, Bloomfield, NJ (US);
James M. Hildreth, Wyckoff, NJ (US)

(73) Assignee: ABB Lummus Global Inc., Bloomfield, NJ (US)

(*) Notice: Subject to any disclaimer, the term of this patent is extended or adjusted under 35 U.S.C. 154(b) by 199 days.

(21) Appl. No.: 10/300,356

(22) Filed: Nov. 20, 2002

(65) Prior Publication Data

US 2004/0094476 A1 May 20, 2004

(51) Int. Cl.[7] .............................................. B01D 11/00
(52) U.S. Cl. ...................... 210/634; 210/639; 210/919; 568/754; 568/758; 585/258
(58) Field of Search ................................. 210/634, 639, 210/908, 909; 568/749, 754, 758; 585/258, 264, 265

(56) References Cited

U.S. PATENT DOCUMENTS

| | | |
|---|---|---|
| 2,807,654 A | 9/1957 | Grimmett et al. |
| 3,300,405 A | 1/1967 | Black |
| 3,446,732 A | 5/1969 | Gasser et al. |
| 3,963,610 A | 6/1976 | Hauschulz et al. |
| 4,016,213 A | 4/1977 | Yeh et al. |
| 4,026,791 A | 5/1977 | Wallace |
| 4,164,469 A | 8/1979 | Wagner |
| 4,179,365 A | 12/1979 | Sumi |
| 4,480,134 A | 10/1984 | Fulmer |
| 4,567,304 A | 1/1986 | Fulmer |
| 4,575,568 A | 3/1986 | Yuhas, Jr. et al. |
| 5,456,806 A | 10/1995 | Lorenzoni et al. |
| 5,905,178 A | 5/1999 | Hildreth |
| 6,071,409 A | 6/2000 | Bondy et al. |
| 6,720,461 B2 * | 4/2004 | Taggart et al. ............... 568/754 |

FOREIGN PATENT DOCUMENTS

| | | |
|---|---|---|
| EP | 0 717 024 A1 | 6/1996 |
| GB | 1459458 | 12/1976 |

OTHER PUBLICATIONS

International Search Report, PCT/US03/36602 filed Nov. 14, 2003.

* cited by examiner

Primary Examiner—Joseph Drodge
(74) Attorney, Agent, or Firm—Dilworth & Barrese, LLP

(57) ABSTRACT

A method is provided herein for the extraction of phenol from a waste water stream. The method is used in conjunction with a process for producing acetone and phenol from cumene. The method for extracting phenol from waste water includes contacting in a countercurrent mode a phenol-containing waste water stream with a hydrocarbon stream derived from a bottoms stream from the acetone finishing column to produce a dephenolated waste water stream and a phenol-containing hydrocarbon stream. The phenol-containing hydrocarbon stream is preferably washed with an aqueous caustic solution to provide a hydrocarbon stream, which is then conveyed to the alpha-methylstyrene recovery system. Preferably the hydrocarbon stream derived from the bottoms stream of the acetone finishing column is water washed prior to contacting the phenol-containing waste water stream.

14 Claims, 4 Drawing Sheets

EXTRACTION OF PHENOL FROM WASTEWATER

BACKGROUND

1. Field of the Invention

The present invention relates to a method for the treatment of aqueous wastes, and particularly to a method for removing phenol from waste water.

2. Background of the Art

Various chemical processes produce waste water streams which contain phenol. For example, in a commonly employed process phenol is produced by the peroxidation of cumene to cumene hydroperoxide, which is then cleaved to phenol and acetone. Alpha-methyl styrene (AMS) is also produced and can be recovered as a by-product, or hydrogenated to cumene and then recycled to the phenol process. Waste water streams from such a process contain dissolved phenol which must be removed before the waste water can be discharged into the environment.

Various methods have been used in the past to remove phenolics (phenol and cresol) from waste water streams, including chemical reaction, adsorption with resins, and liquid-liquid extraction.

In extraction processes the phenol-containing water is treated with an extractant. Typically, the extractant is a solvent which is immiscible in water, but in which the phenol preferably dissolves. The phenol is thereafter recovered from the extractant stream. Various extractants have been employed, including benzene, toluene, xylene, cumene, and other aromatic or aliphatic liquids.

For example, U.S. Pat. No. 3,963,610 to Hauschulz et al. discloses a method of removing phenol from wastewater using cumene as an extractant. The cumene is washed with aqueous sodium carbonate and then sodium hydroxide to recover the phenol as a phenate.

U.S. Pat. No. 6,071,409 to Bondy et al. discloses phenolic wastewater treatment with ethers for removal and recovery of phenolics.

In a conventional method, aqueous effluent containing phenol is treated with solvent extraction to remove phenol in a single-stage extraction method which includes recycling of the solvent. The fresh solvent is supplied from an overhead of an AMS topping column and includes cumene and other hydrocarbons. The phenol is recovered from the solvent by caustic washing and is then recycled back to the process.

More particularly, referring now to FIG. 1, a prior art system 10 for the recovery of phenol and acetone from the product of the oxidation and cleavage of cumene is shown. Methods and apparatus for oxidizing cumene to cumene hydroperoxide and cleaving the cumene hydroperoxide to acetone and phenol are known. Effluent 11 from the cleavage of cumene hydroperoxide contains acetone, phenol, and by-products such as cumene, AMS, and other components (e.g., benzene, toluene, ethylbenzene, butyl benzene). The effluent 11 is sent to a splitter 12 which separates by fractionation an overhead stream 13 containing acetone, cumene and AMS, and a bottoms stream 14 containing phenol and some AMS. The bottoms 14 is sent to distillation column 21 wherein AMS is separated out as an overhead stream 22 and phenol and other heavier components are separated out as a bottoms stream 23. The bottoms stream 23 is then sent on to further purification in distillation column 24 wherein purified phenol is separated as an overhead stream 25 and heavier components are separated out as a bottoms stream 26.

The overhead stream 13 from splitter 12 is sent to distillation system 15 wherein acetone is separated out as an overhead stream 16, and cumene and AMS are separated out as a bottoms stream 17. The bottoms stream 17 is sent to distillation system 18, which separates the cumene-AMS mixture by fractionation into an overhead stream 19 containing cumene and other components, and a bottoms stream 20 containing AMS.

The overhead from the distillation system 18 is then sent to prior known system 50 for recovery of phenol from waste water. Referring now to FIG. 2, waste water stream 52 is introduced into a primary dephenolation drum 51. The waste water stream may optionally be pre-treated with acid (e.g., $H_2SO_4$) to convert any phenates in the water to phenol, which can be removed by the hydrocarbon extractant. Stream 19 containing cumene and other hydrocarbons is introduced into drum 51 and the dephenolated water is discharged via stream 53. The hydrocarbon solvent stream, which contains a major portion of the phenol, is sent via stream 55 to caustic wash drum 56. Caustic solution (e.g., 20% aqueous NaOH) is added to the drum via stream 57 to convert phenol back into a phenate (sodium phenate) which is preferentially soluble in water and thereafter removed in water stream 58. A portion of stream 58 may optionally be recycled to stream 57. The hydrocarbon stream, is removed via stream 59. A portion of the hydrocarbon solvent is recycled via stream 54 back to stream 19. Another portion 60 is sent on to further processing.

What is needed is an improved method for extracting phenol from a wastewater stream which can be used in conjunction with a process for producing phenol and acetone from cumene.

SUMMARY OF THE INVENTION

A method is provided herein for the extraction of phenol from a waste water stream. The method is used in conjunction with a process for producing acetone and phenol from cumene which includes an acetone finishing column and an alpha-methylstyrene recovery system downstream of the acetone finishing column. The method for extracting phenol from waste water comprises contacting a phenol-containing waste water stream with a fresh hydrocarbon solvent, the hydrocarbon solvent being a hydrocarbon portion of a bottoms stream from the acetone finishing column, to produce a dephenolated waste water stream and a spent hydrocarbon solvent; and, conveying at least some of the spent hydrocarbon solvent to the alpha-methylstyrene recovery system without recycling any portion of the spent hydrocarbon solvent to the step (a) of contacting the phenol-containing waste water. Preferably, a major portion of phenol in the spent hydrocarbon is removed, for example by caustic washing, prior to step of conveying the spent hydrocarbon solvent to the alpha-methylstyrene recovery system.

Preferably the fresh hydrocarbon stream derived from the bottoms stream of the acetone finishing column is water washed prior to contacting the phenol-containing waste water stream in order to remove any entrained phenate.

The method and system of the present invention advantageously provides significantly better phenol recovery from the waste water than the prior known method.

BRIEF DESCRIPTION OF THE DRAWINGS

Various embodiments are described herein with reference to the drawings wherein.

DETAILED DESCRIPTION OF PREFERRED EMBODIMENT(S)

Figure 3:
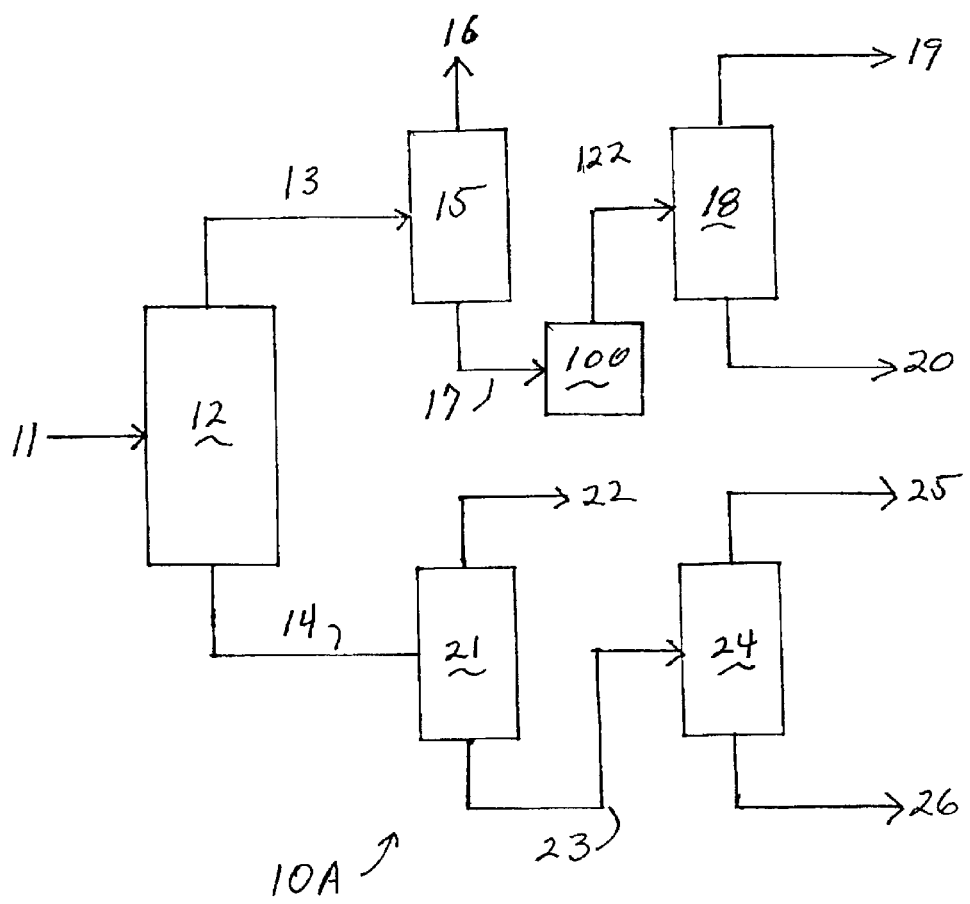
FIG. 3 is a schematic flow chart of a system for recovery of phenol and acetone in a cumene oxidation process, which incorporates the system of the invention for extracting phenol from waste water; and, FIG. 4 is schematic flow chart of a system of the present invention for extracting phenol from waste water.

Referring now to FIG. 3, a process 10A for the recovery of phenol and acetone from the product of the oxidation and cleavage of cumene is shown. Process 10A incorporates the phenol recovery system 100 of the present invention. Numerals similar to those of FIG. 1 indicate similar items. As can be seen, phenol recovery system employs the upstream bottoms 17 from the acetone finishing column 15, rather than the downstream overhead 19 of the AMS recovery system 18. The acetone finishing column separates acetone into an overhead stream 16 and higher boiling components including AMS and cumene into the bottoms stream 17. This new arrangement provides the advantage of a greater flow of upstream hydrocarbon solvent, which eliminates the need for recycling of solvent in the phenol recovery system 100. Thus, only fresh hydrocarbon is used as an unrecycled "once through" solvent, and lower phenol content of the treated waste water is attainable. "Fresh" hydrocarbon solvent is that which has not yet been used in the contacting step to recover phenol from the waste water. "Spent" hydrocarbon solvent is that which has been contacted with the waste water in the contacting step.

Figure 4:
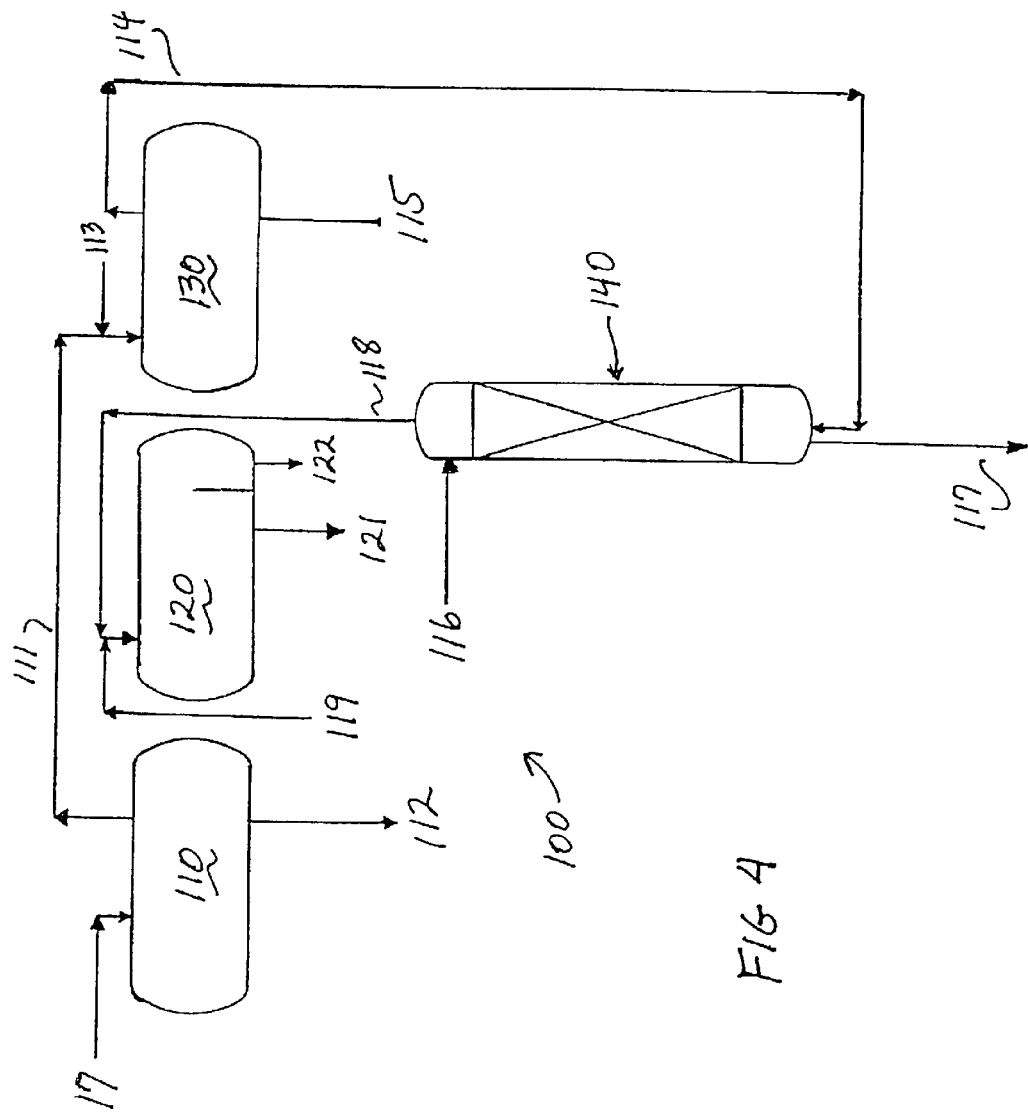

Referring to FIG. 4, a flow diagram of system 100 for the recovery of phenol from a waste water stream is illustrated. The system 100 includes a solvent extraction apparatus in which the wastewater is contacted with an organic solvent in which the phenol preferentially dissolves. Preferably, the fresh hydrocarbon solvent is derived from the bottoms (stream 17) of an acetone finishing column, as described above. Stream 17 includes cumene, alpha-methylstyrene ("AMS"), minor amounts of other aromatics and acetone, and some water, and is introduced into a settling tank 110 wherein the water settles to the bottom and is drawn off as an aqueous purge 112. The organics, i.e., cumene and AMS, are transferred via stream 111 to solvent wash drum 130 wherein water condensate is added via stream 113. Traces of entrained phenate and/or acetone are washed out with waste water in stream 115. The solvent wash is generally conducted at a temperature of from about 30° C. to about 50° C., preferably from about 40° C. to about 45° C.

The washed fresh hydrocarbon solvent is then transferred via stream 114 to the phenol extraction column 140, which operates in a countercurrent mode. Phenol-containing waste water is introduced at the top of column 140 via stream 116 and moves downward. Column 140 is preferably a packed column containing one or more beds of packing. The phenol content of the waste water is generally above 1,000 ppm and typically ranges from about 5,000 ppm to 10,000 ppm. The waste water can optionally be pre-treated with acid (e.g., $H_2SO_4$) to convert any phenates to phenol, which is then removed by the hydrocarbon solvent. The solvent, which includes washed cumene and AMS, enters the bottom of column 140 and rises upward because of its lighter density. The effluent waste water, from which the phenol is removed, is drawn off via stream 117, and can typically have a residual phenol content of no more than about 100 ppm. The countercurrent solvent extraction of phenol is preferably conducted at a temperature ranging from about 30° C. to about 50° C., more preferably from about 35° C. to about 40° C.

The spent solvent, containing the extracted phenol, is transferred via stream 118 to caustic wash drum 120. Caustic, such sodium hydroxide solution (e.g., 20% by weight NaOH), is added via stream 119. At least a major portion of the phenol in the spent hydrocarbon solvent reacts with the caustic to produce a phenate (e.g., sodium phenate), which is then withdrawn in a phenate-containing aqueous stream 121. The spent hydrocarbon solvent, containing mostly cumene and AMS, is withdrawn from the caustic wash drum 120 via stream 122. Preferably the entire portion of the spent hydrocarbon solvent is sent to further recovery, i.e., the AMS recovery system 18. No portion of the spent hydrocarbon solvent stream is recycled back for waste water dephenolation in column 140.

The Example and Comparative Example below illustrate, respectively, the system of the present invention and a prior known system, and demonstrate the superiority of the system of the present invention.

EXAMPLE

A mass balance was constructed for a system as shown in FIGS. 3 and 4 for the recovery of phenol from waste water. Conventional processing equipment was employed. The mass balance as set forth in Table 1 includes mass flow rates in kg/hr and composition weight percentages in parentheses. The following streams are surveyed:

111—hydrocarbon solvent stream introduced into the solvent wash tank 130.

114—hydrocarbon solvent stream from the wash tank 130 and flowing into the countercurrent solvent extraction column 140.

118—hydrocarbon solvent stream exiting the solvent extraction column 140 with extracted phenol.

116—phenol-containing waste water stream introduced into the solvent extraction column 140.

117—dephenolated waste water stream exiting the solvent extraction column.

TABLE 1

|  | 111 | 114 | 118 | 116 | 117 |
|---|---|---|---|---|---|
| Other Aromatics* | 46.7 (0.30%) | 46.7 (0.30%) | 46.7 (0.29%) | — | — |
| AMS | 3,767.9 (23.84%) | 3,767.9 (23.84%) | 3,767.9 (23.65%) | — | — |
| Water | — | — | — | 16,518.4 (94.95%) | 16,518.4 (95.68%) |
| Acetone | 8.40 (0.05%) | 8.4 (0.05%) | 8.4 (0.05%) | 86.4 (0.50%) | 86.4 (0.50%) |
| Phenol | — | — | 132.1 (0.83%) | 133.5 (0.77%) | 1.38 (0.01%) |
| Cumene | 11,979.3 (75.81%) | 11,979.3 (75.81%) | 11,979.3 (75.18%) | — | — |
| Na Phenate | — | — | — | — | — |
| Other** | 0.10 (<0.001%) | 0.10 (<0.001%) | 0.10 (<0.001%) | 657.8 (3.78%) | 657.8 (3.81%) |
| Total | 15,802.4 (100.00%) | 15,802.4 (100.00%) | 15,934.4 (100.00%) | 17,396.1 (100.00%) | 17,263.9 (100.00%) |

*Benzene, toluene, ethylbenzene, butylbenzene.
**Various salts and other components.

As can be seen the phenol content of the waste water stream is reduced from 0.77% (7,700 ppm) to 0.01% (100 ppm).

COMPARATIVE EXAMPLE

Figure 1:
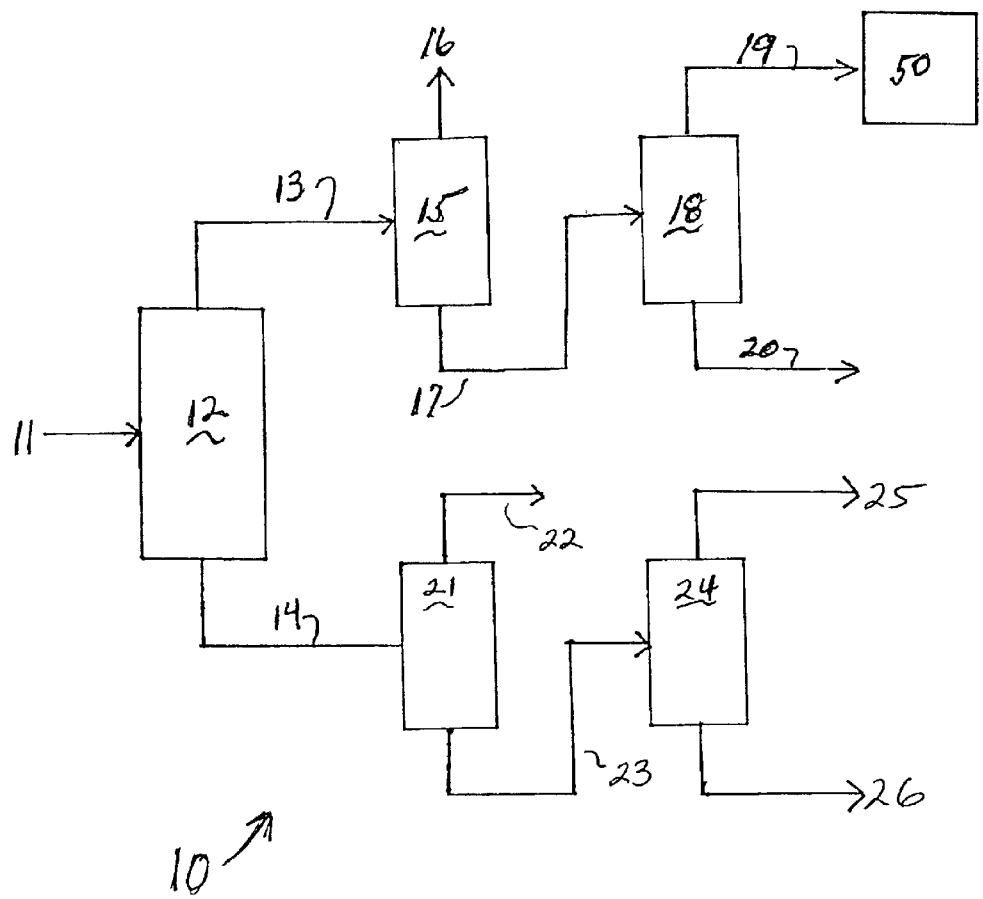
FIG. 1 is a schematic flow chart of a prior art system for recovery of phenol and acetone in a cumene oxidation process, which incorporates a system for extracting phenol from a waste water stream.
Figure 2:
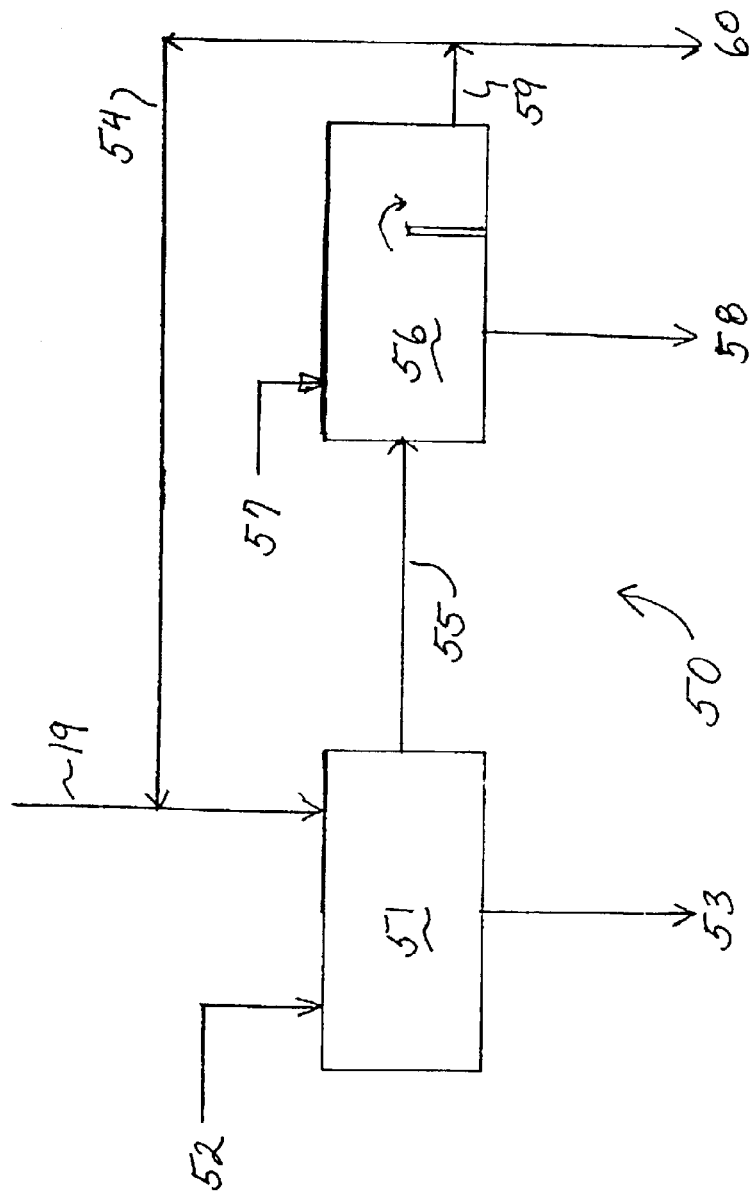
FIG. 2 is schematic flow chart of a known system for extracting phenol from waste water.

A mass balance was constructed for a system as shown in FIGS. 1 and 2 for the recovery of phenol from waste water.

Conventional processing equipment was employed. The mass balance as set forth in Table 2 includes mass flow rates in kg/hr and composition weight percentages in parentheses. The following streams are surveyed:

19—hydrocarbon solvent overhead from the AMS topping column (portion of the reflux).

54—hydrocarbon solvent recycle stream from the caustic wash tank 56.

55—hydrocarbon solvent stream exiting the solvent extraction tank 51 with extracted phenol.

52—phenol-containing waste water stream introduced into the solvent extraction tank 51.

53—dephenolated waste water stream exiting the solvent extraction tank 51.

TABLE 2

|  | 19 | 54 | 55 | 52 | 53 |
|---|---|---|---|---|---|
| Other Aromatics* | 13.2 (26.04%) | 10,312.5 (32.5%) | 10,325.7 (32.40%) | — | — |
| AMS | — | — | — | — | — |
| Water | — | — | — | 10,604.1 (95.68%) | 10,604.1 (96.46%) |
| Acetone | 1.4 (2.76%) | 321.1 (1.01%) | 323.4 (1.01%) | 45.5 (0.41%) | 44.6 (0.41%) |
| Phenol | — | 15.9 (0.05%) | 113.6 (0.36%) | 108.9 (0.98%) | 11.2 (0.10%) |
| Cumene | 30.4 (59.96%) | 16,675.2 (52.55%) | 16,696.6 (52.38%) | — | 9.0 (0.08%) |
| Na Phenate | — | — | — | — | — |
| Other** | 5.7 (11.24%) | 4,408 (13.89%) | 4413.6 (13.85%) | 324.2 (2.93%) | 324.2 (2.95%) |
| Total | 50.7 (100.00%) | 31,732.7 (100.00%) | 31,872.9 (100.00%) | 11,082.7 (100.00%) | 10,993.1 (100.00%) |

*Benzene, toluene, ethylbenzene, butylbenzene.
**Various salts and other components.

As can be seen from TABLE 1 and TABLE 2, the dephenolated waste water (stream 117) from the system of the present invention contains only 0.01% phenol, i.e., 100 ppm. Dephenolated waste water stream 53 of the prior method contains 0.1% phenol, i.e., 1,000 ppm. The prior known method requires a high volume of recycle of the solvent extractant. However, the caustic washed solvent (recycle stream 54) still retains an equilibrium amount of 0.05% phenol (500 ppm) which limits the effectiveness of the dephenolation of the waste water. In contrast to the prior known system, the system of the present invention is incorporated upstream of the AMS recovery system and includes a "once through" unrecycled solvent system. The upstream location provides access to a large amount of fresh hydrocarbon from the bottoms of the acetone finishing column for use as a solvent extractant, thereby eliminating the need for solvent recycle within the waste water dephenolation system. Thus, the method of the present invention achieves significantly better results.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. In a process for producing acetone and phenol from cumene which includes an acetone finishing column and an alpha-methylstyrene recovery system downstream of the acetone finishing column, a method for extracting phenol from waste water which comprises:

a) contacting a phenol-containing waste water stream with a fresh hydrocarbon solvent, said hydrocarbon solvent being a hydrocarbon portion of a bottoms stream from the acetone finishing column, to produce a dephenolated waste water stream and a spent hydrocarbon solvent; and, b) conveying at least some of the spent hydrocarbon solvent to the alpha-methylstyrene recovery system without recycling any portion of the spent hydrocarbon solvent to the step (a) of contacting the phenol-containing waste water.

2. The method of claim 1 wherein the spent hydrocarbon solvent produced in contacting step (a) contains phenol and the method further includes the step of:

removing a major portion of the phenol from the spent hydrocarbon solvent prior to step (b) of conveying the spent hydrocarbon solvent to the alpha-methylstyrene recovery system.

3. The method of claim 2 wherein the step of removing a major portion of the phenol comprises washing the phenol-containing spent hydrocarbon solvent with an aqueous caustic solution.

4. The method of claim 3 wherein the aqueous caustic solution comprises 20% sodium hydroxide.

5. The method of claim 2 wherein substantially all of the spent hydrocarbon solvent is conveyed to the alpha-methylstyrene recovery system.

6. The method of claim 1 wherein the fresh hydrocarbon solvent is water washed prior to contacting the phenol-containing waste water stream.

7. The method of claim 1 wherein the fresh hydrocarbon solvent contains cumene and alpha-methylstyrene.

8. The method of claim 1 wherein the waste water is pre-treated with acid prior to the contacting step (a) to convert phenates to phenol.

9. The method of claim 1 wherein the contacting step (a) is conducted in a column containing at least one packed bed.

10. The method of claim 9 wherein the contacting step (a) is performed in a countercurrent mode.

11. The method of claim 1 wherein the contacting step (a) is performed at a temperature of from about 30° C. to about 50° C.

12. In a process for producing acetone and phenol from cumene which includes an acetone finishing column and an alpha-methylstyrene recovery system downstream of the acetone finishing column, a method for extracting phenol from waste water which comprises:

a) contacting in a counter current mode a phenol-containing waste water stream with a fresh hydrocarbon solvent, said hydrocarbon solvent being a hydrocarbon portion of a bottoms stream from the acetone finishing column, to produce a dephenolated waste water stream and a phenol-containing spent hydrocarbon solvent;

b) removing a major portion of the phenol from the spent hydrocarbon solvent to provide a dephenolated spent hydrocarbon solvent; and, c) conveying the dephenolated spent hydrocarbon solvent to the alpha-methylstyrene recovery system without recycling any portion of the spent hydrocarbon solvent to the step (a) of contacting the phenol-containing waste water.

13. The method of claim 12 wherein the step (b) of removing a major portion of the phenol comprises washing the phenol-containing spent hydrocarbon solvent with an aqueous caustic solution.

14. The method of claim 13 wherein the aqueous caustic solution comprises 20% sodium hydroxide.

* * * * *